US 6,475,756 B1

(12) United States Patent
Wirth et al.

(10) Patent No.: US 6,475,756 B1
(45) Date of Patent: Nov. 5, 2002

(54) DEVELOPMENT OF VIRUSES RESISTANT TO INACTIVATION BY THE HUMAN COMPLEMENT SYSTEM

(75) Inventors: Dagmar Wirth; Dirk Spitzer; Hansjoerg Hauser, all of Braunschweig (DE)

(73) Assignee: Gesellschaft fuer Biotechnologische Forschung mbH(GBF), Braunschweig (DE)

( * ) Notice: Subject to any disclaimer, the term of this patent is extended or adjusted under 35 U.S.C. 154(b) by 0 days.

(21) Appl. No.: 09/554,838
(22) PCT Filed: Nov. 20, 1998
(86) PCT No.: PCT/EP98/07484
§ 371 (c)(1), (2), (4) Date: Jul. 21, 2000
(87) PCT Pub. No.: WO99/27121
PCT Pub. Date: Jun. 3, 1999
(51) Int. Cl.$^7$ ............... C12P 21/04; C12Q 1/70; A61K 39/00; C07H 21/04
(52) U.S. Cl. ............... 435/69.7; 435/5; 424/192.1; 536/23.4
(58) Field of Search ............... 536/23.4; 434/192.1; 435/5, 69.7

(56) References Cited

PUBLICATIONS

References cited in the PCT application have been considered.*

* cited by examiner

*Primary Examiner*—Hankyel T. Park
(74) *Attorney, Agent, or Firm*—Frommer Lawrence & Haug LLP; Ronald R. Santucci

(57) ABSTRACT

Murine retroviruses are the most important transfer systems for human gene therapy. However, their application is currently limited. One of the major restrictions both for an application in vivo resides in the problem that this virus type is sensitive to inactivation by human complement factors. Our invention overcomes this limitation. We have modified murine recombinant retroviruses in a way that they are resistant to human complement factors. This was achieved by genetic modification of the retroviral surface protein env which is responsible for receptor interaction: the receptor interacting domain of env was fused to catalytically active domains of human complement inactivation factors. These modified env were expressed in complement-sensitive cells and specifically integrated into virus particles. By this strategy cells and viruses are generated that are fully resistant to complement attack. Thus, this strategy provides a tool for establishment of complement resistant cells and generation of viruses for in vivo gene therapy.

20 Claims, 7 Drawing Sheets

Figure 1:
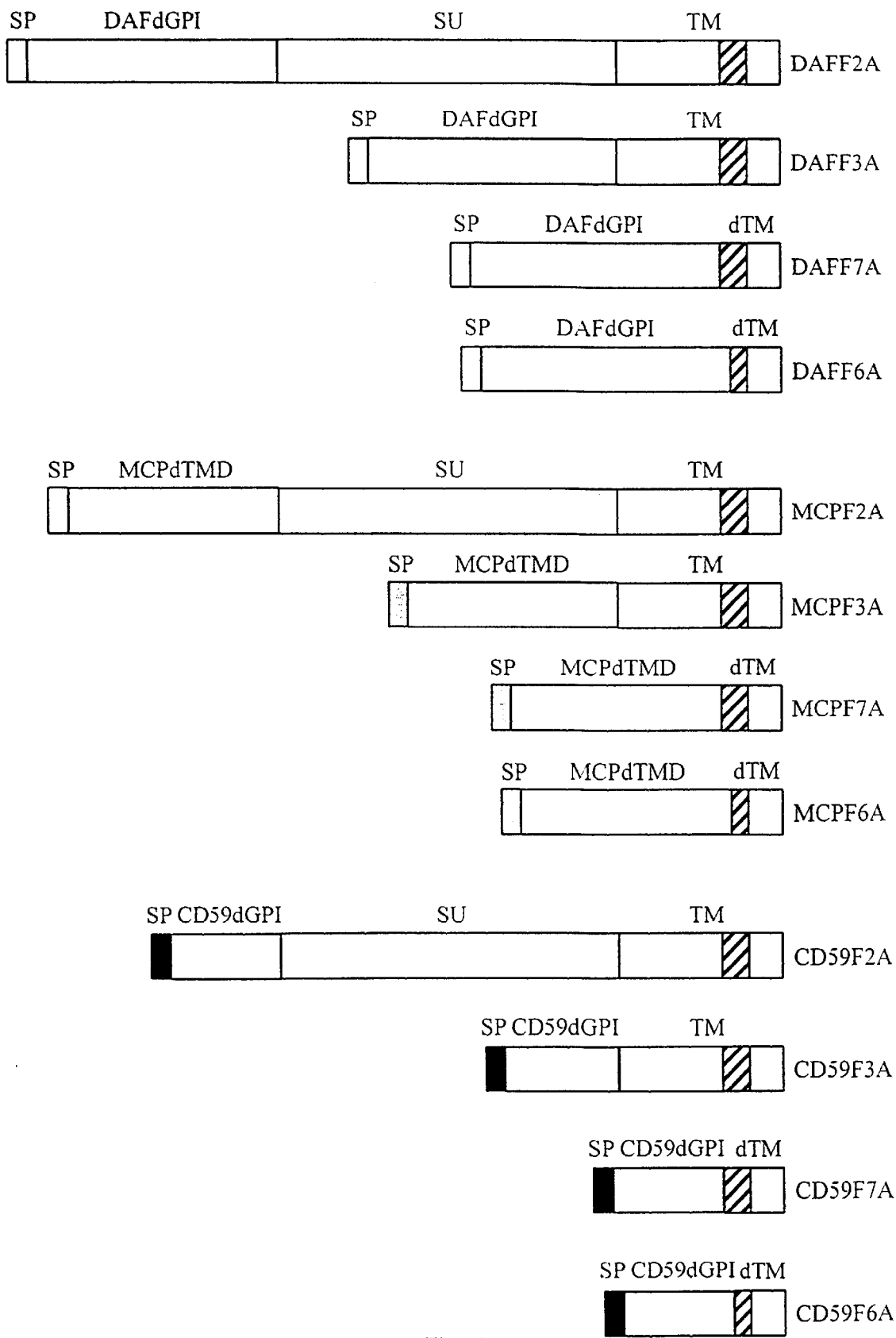
Figure 2A:
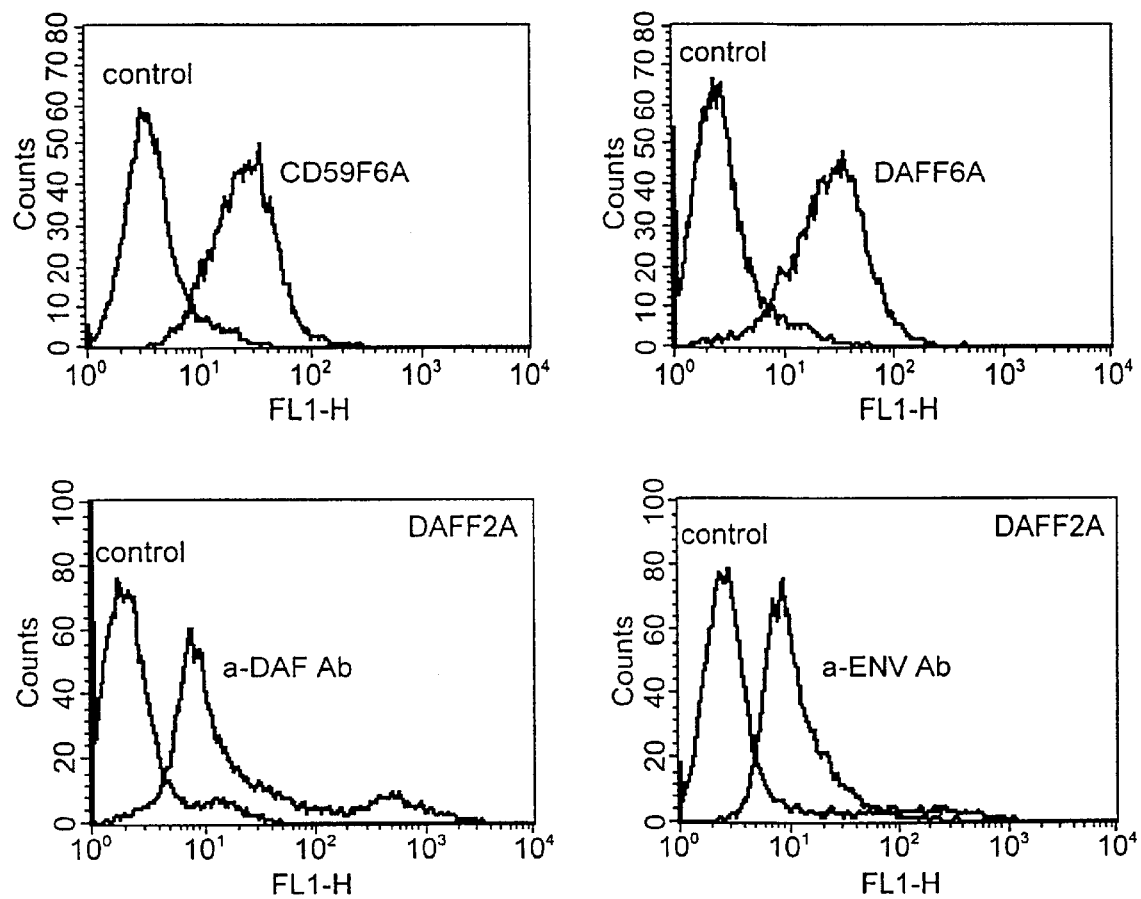
Figure 2B:
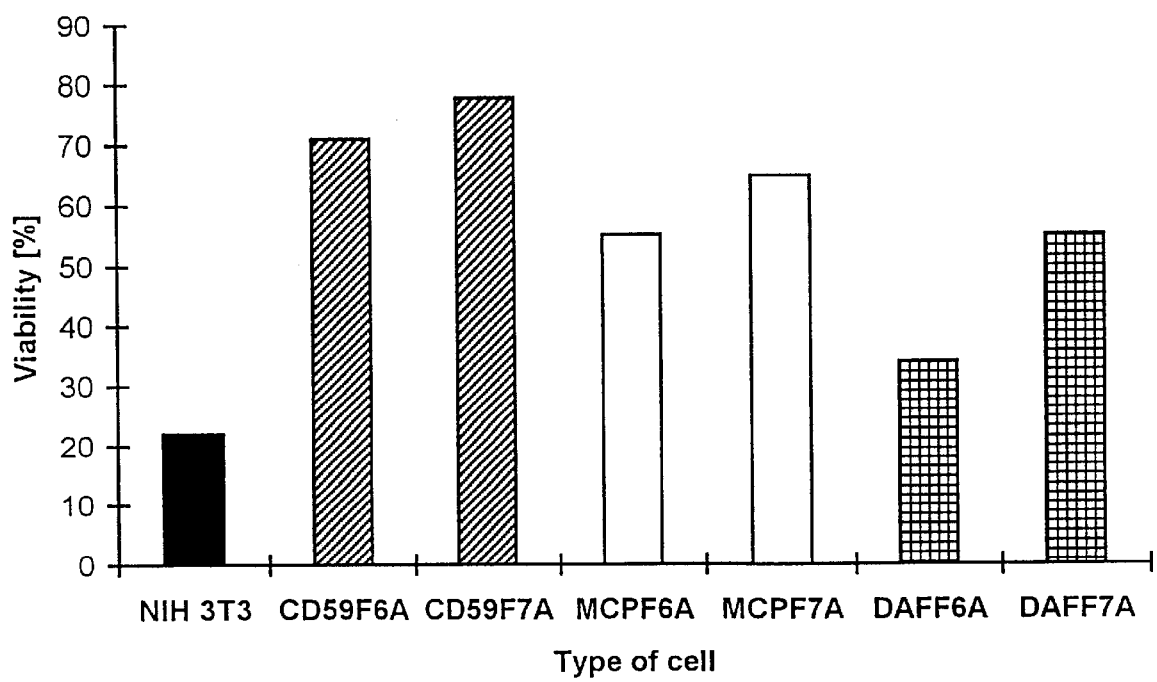
Figure 3A:
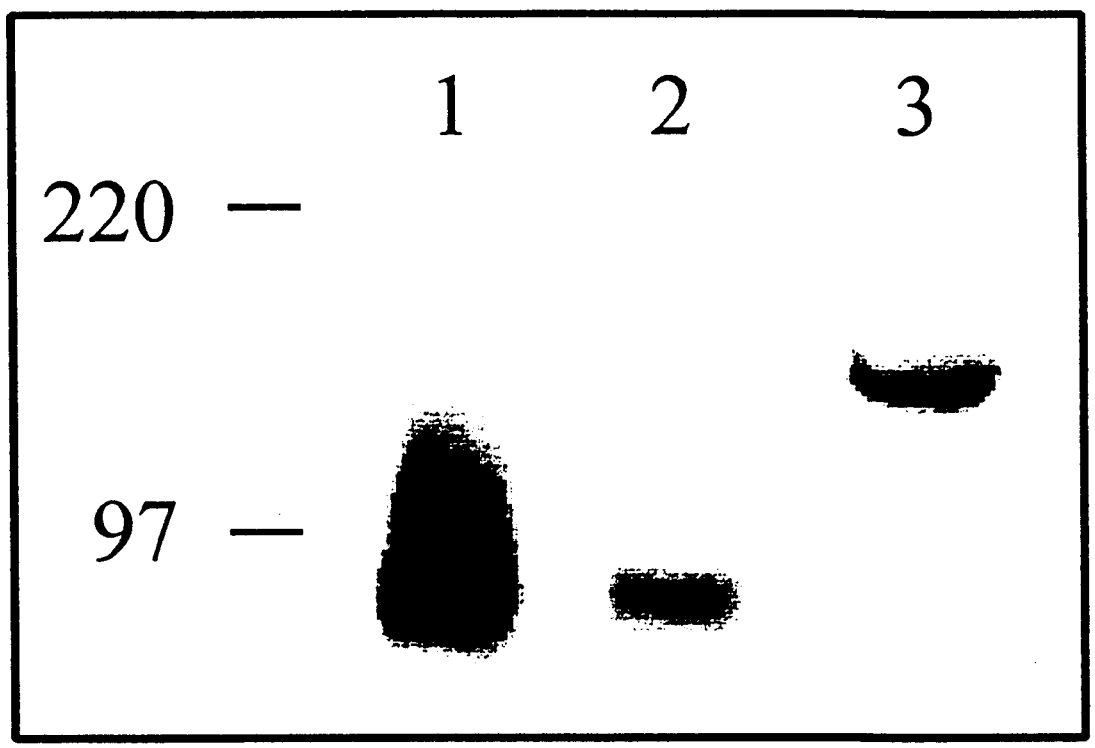
Figure 4:
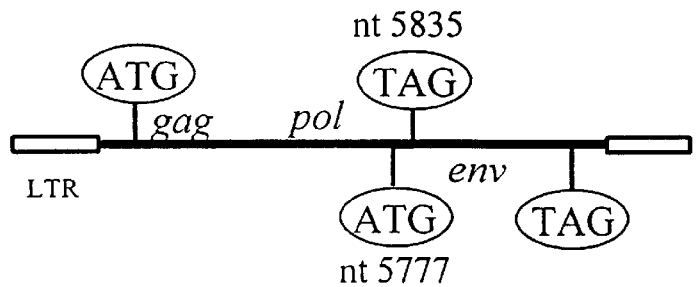
Figure 4:
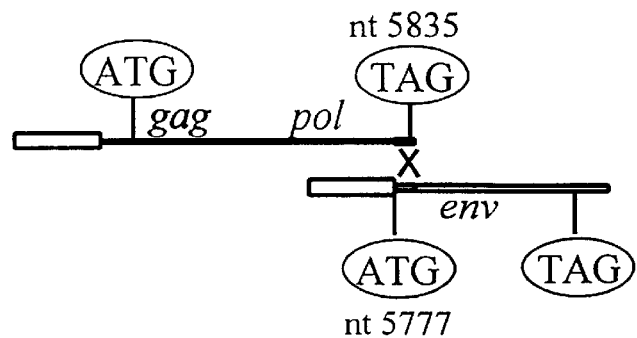
Figure 4:
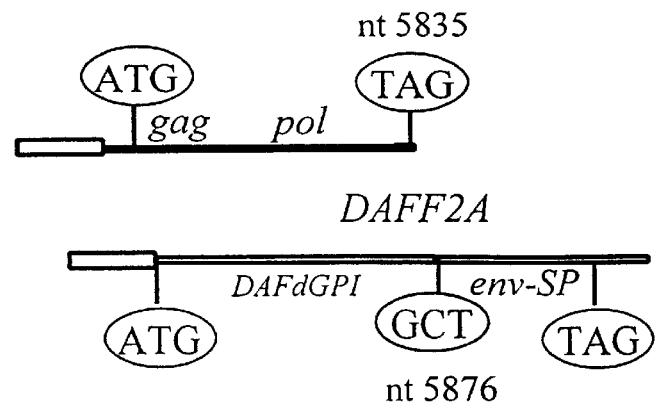

DAFF2A is integrated into the retroviral membrane as a fusion protein

Fig. 3b

Fig. 3c

Wild type virus genome

Classical packaging cell

Packaging cell using DAFF2A fusion protein

DEVELOPMENT OF VIRUSES RESISTANT TO INACTIVATION BY THE HUMAN COMPLEMENT SYSTEM

STATE OF THE ART

1. Biology of Murine Retroviruses

Murine retroviruses carry three genes (gag, pol, env) encoding polyproteins essential for virus formation and infection. The gag gene encodes structural proteins for virus inner capsid formation, pol provides the enzymatic proteins needed for processing viral proteins, for reverse transcription of packaged RNA molecule(s) and finally for integration of the provirus. The env gene encodes a polyprotein which is transferred via the endoplasmatic reticulum, proteolytically processed and glycosylated by cellular enzymes and finally integrated into the cellular membrane. It consists of different domains: A signal peptide which is cleaved off after transport to the endoplasmatic reticulum, an extracellular surface domain (SU) and a transmembrane domain (TM) which is both noncovalently and via S bridges bound to SU and thereby anchoring the protein complex within the cellular membrane. SU is cleaved from TM by a cellular protease during transport/processing of the polyprotein through the secretory pathway.

In a final step of virus release from the cell, retrovirus particles are formed by assembly of gag and gagpol proteins at sites of the cellular membrane which are covered with env proteins; it has been shown for certain virus types that the intracellular part of TM is interacting with the MA domains of gag polyproteins (Brody et al., 1994; Dorfman et al., 1994) and is thereby involved in the specific integration of env proteins. Subsequently, budding of virus capsids takes place through the cellular membrane. As a result, retrovirus particles are enveloped by cellular membrane and spiked with homotrimers of env proteins. While retroviral env proteins are highly represented in virus membranes, a similar abundance has not been shown for any cellular surface marker. Thus, in contrast to specific env the incorporation of cellular proteins into virus outer membrane is assumed to be random.

During the process of infection, the SU protein is required for interaction with the respective receptor while the TM protein is responsible for subsequent fusion of the virus particle with the interacting cell.

2. Retroviruses for Gene Transfer and Packaging Cells

For gene transfer modified retroviruses are used which have been immobilised and therefore cannot leave the host cell. However, they still express the respective viral genes. In these so-called packaging or helper cells the retroviral transcription unit has been modified by deletion of the packaging sequence required for specific incorporation of viral RNA into the virus particles, a sequence that provides transmission of the retroviral genome in wild type viruses. By transfection of packaging cells with retroviral vectors carrying the respective therapeutic gene and the packaging sequence recombinant virus particles are formed. Since the viral genes themselves have been immobilized, only the vector RNA is packaged into the virus particle and transduced to the infected cell.

3. Alteration of Virus Tropism by Genetic Modifications of env

During the last years, much effort has been undertaken to modify the host range of retroviruses by alteration of the retroviral env protein. Many attempts have been undertaken to create functional, i.e. infectious fusion proteins for retroviruses. Most of them failed. Several groups could show that N-terminal tagging of SU is possible. Although redirection of viruses to other cellular receptors has not been achieved with murine retroviruses to date, in some cases a tag on env does not inhibit receptor interaction.

4. The Complement System

One of the mechanisms of human defense invading organisms attack is the complement mediated lysis of invading organisms. The complement mediated inactivation is a multistep enzymatic cascade which finally results in formation of a membrane attack complex (MAC) mediating the perforation of membranes and subsequent lysis of the invading organism. It is either initiated by antigen-antibody complexes (classical pathway) or via an antibody independent pathway which is activated by certain particular polysaccharides, viruses and bacteria (alternative pathway).

Human organs and cells themselves are protected to complement mediated lysis. This protection is achieved by expression of so-called complement inactivation factors. So far, five human factors are known; CD35 (CR1) is released from the cells and acts mainly extrinsically. In contrast, CD59, CD46 (MCP), CD55 (DAF) and HRF are integrated into the cellular membrane: CD46 (MCP) is a classical transmembrane protein while HRF, CD59 and CD55 are GPI-anchored. These factors can interrupt the complement cascade at two different stages: DAF, CR1 and MCP act at an early stage of both the alternative and the classical pathway; in contrast, CD59 and HRF inhibit the assembly of the membrane attack complex which is the final step of both pathways resulting in channel formation and lysis.

Viruses with a natural human host range have developed strategies to overcome this defense system. So for Herpes Saimiri it has been reported that this virus has overcome complement mediated lysis by presenting a virus encoded complement control protein homolog (CCPH) (Fodor et al., 1995), which is also able to block the cascade at the early stage. HIV can incorporate cellular DAF, MCP, and CD59 at levels that protect from complement-mediated destruction (Saifuddin et al., 1995; 1997).

5. Human Complement Mediated Inactivation of Mouse Retroviruses

Early investigations provided evidence that murine retroviruses are inactivated via the complement mediated attack (Welsh et al., 1975). At that time, evidence was given that the cascade is started by direct binding of the extracellular domain of the TM domain to C1, the first enzyme of the classical pathway, resulting in a direct, immunoglobulin independent activation of the classical pathway (Cooper et al., 1976; Bartholemew et al., 1980). Meanwhile, an additional reason for complement instability of mouse retroviruses became apparent (Rother et al., 1995; Takeuchi et al., 1996): natural human antibodies directed against the α-galactosyl epitope presented by non-old world primate cells have been shown to be responsible for complement mediated inactivation via the alternative pathway. Thus, the glycosylation pattern of the host cell is believed to contribute to the complement sensitivity of retroviruses generated thereof. Indeed, murine retroviruses produced from certain human cell lines are stable against complement mediated attack (Cosset et al., 1995). However, in spite of this altered glycosylation, not all human cells are suitable to provide this protection (Takeuchi et al., 1994) indicating that the problem of complement mediated lysis cannot be not exclusively deduced to this specific glycosylation pattern. Thus, TM mediated activation of complement and/or other, still unknown mechanism might contribute to the formation of complement sensitive viruses even from human cells.

Thus, the invention concerns a ssDNA or dsDNA encoding a fusion protein of
- a retroviral surface protein (ENV) or a part thereof comprising its transmembrane domain and
- a catalytically active domain of a complement inactivation factor.

As regards an ENV part, it should be kept in mind, as already mentioned before, that an extracellular surface domain (SU) is required for interaction with the respective receptor; cf. also Examples on FIGS. 1 to 4.

The ssDNA or dsDNA according to the invention can be characterized in that the catalytically active domain of the complement inactivation factor is fused with its N-terminus to the C-terminus of the retroviral surface protein (ENV) or its part.

Further, the ssDNA or dsDNA according to the invention can be characterized by a human complement inactivation factor, especially DAF, CD 59, MCP or HRF; or a virus complement inactivation factor, especially CCPH.

Further, the ssDNA or dsDNA according to the invention can be characterized by a retroviral SU protein, a retroviral TM protein or parts of these protein, especially amphotropic ENV 10 A 1, ENV 4070 A, ecotropic ENV, GALV ENV or chimeras thereof.

Concerned is further a ssDNA or dsDNA according to the invention which offers a virus or a cell, especially a packaging cell, stability against a complement system, especially a human complement system, and is obtainable by subjecting viruses or cells, especially packaging cells, which are characterized by a fusion protein as defined by any of the preceding claims to a complement system, especially a human complement system, selecting a virus or a cell which remains stable and identifying and isolating said ssDNA or dsDNA from said virus or cell.

Further, the invention concerns a fusion protein encoded by a ssDNA or dsDNA according to the invention.

Further, the invention concerns a virus which is transduction efficient and stable against the human complement system, characterized by at least one fusion protein according to the invention as envelope protein.

The virus according to the invention can be characterized in that the virus is a retrovirus, especially a murine virus, is a virus other than a retrovirus, is a composite virus or is a pseudotyped virus.

Further, the invention concerns a packaging cell for the production of a virus according to the invention, characterized by an integrated or unintegrated dsDNA according to the invention.

Further, packaging cell according to the invention can be characterized in that it is a human cell or a non-human cell, especially a murine cell.

Further, the packaging cell according to the invention can be characterized in that it comprises in addition a dsDNA encoding a wild-type retroviral envelope protein or a part thereof comprising its receptor interacting domain.

Further the packaging cell according to the invention can be characterized in that it is derived from a known packaging cell, especially PA 317 or GP+AM 12.

Further, the invention concerns a use of a virus according to the invention for the enhancement of the transduction efficiency of viruses for human gene therapy.

Further, the invention concerns a use of a fusion protein according to the invention for the generation of complement resistant cells for transplantation.

Further, the invention concerns a use of a fusion protein according to the invention for the reduction of the risk of a formation of replication competent viruses by means of packaging cells via recombination by eliminating the intrinsic sequence overlap of retroviral gagpol and env genes.

Further, the invention concerns a use of a fusion protein according to the invention for generating complement stabilized packaging cells by coexpression of wild-type ENV proteins and fusion proteins according to the invention.

Further, the invention concerns a use of a fusion protein according to the invention for generating complement stabilized viruses according to the invention.

EXAMPLES

FIG. 1

Construction of fusion proteins comprising catalytically active domains of complement inactivation factors (DAF, MCP and CD59 as indicated) and different domains of retroviral env proteins (hatched: SU, white: TM; bright hatched: transmembrane domain of TM)

FIG. 2

Expression of fusion proteins can overcome complement-mediated lysis of cells

Mouse NIH3T3 cells were stably transfected with different fusion genes. Cell surface expression was confirmed by FACS analysis (a); complement stability was determined in a viability assay (b).

a) FACS analysis of transfected (thick line) and non-transfected (thin line) cells was performed using antibodies directed against the respective human complement inactivation factors.

b) Transfected and non-transfected cells were incubated with human serum samples providing active or heat-inactivated complement resistance factors. Subsequently, viability was determined by trypan blue dye exclusion assay. The relative numbers of living cells obtained from the active serum samples and from the inactivated samples is given as % viability.

FIG. 3

Expression of DAFF2A in gagpol expressing cells results in formation of infective retroviruses which are resistant to complement-mediated lysis Wild type env and DAFF2A, respectively, was stably transfected into GP-pac cells (NIH3T3 cells expressing retroviral gagpol gene and a retroviral vector confering resistance to puromycin). The titer was determined to $1\times10^5$ cfu/ml for DAFF2A transfected cells and $2–9\times10^5$ cfu/ml for control cells transfected with wild type env.

a) Virus particles were collected and subjected to Western analysis using an anti-env antibody lane 1: Virus particles generated from PA317 packaging cells expressing wild type env antibody lane 2: virus particles generated from GP-pac cells transfected with wild type env lane 3: virus particles generated from GP-pac cells transfected with DAFF2A b) Virus particles generated from GP-pac+env (white bars) and GP-pac+DAFF2A cells (black bars) were incubated with active and heat-inactivated human serum from different donors (1, 3, 7 and a pool) and the infectious titer was determined. The number of clones obtained from viruses incubated with heat-inactivated serum samples was set to 100 and the number of clones obtained from active serum samples are given as % stability.

c) Protection of DAFF2A viruses against complement lysis can be eliminated by blocking the catalytically active domain.

Viruses obtained from GP-pac cells transfected with wild type env (white bars) and DAFF2A (black bars) were incubated with an anti DAF antibody prior to incubation with active and inactive serum samples. The stability of viruses was determined as indicated above. Incubation of DAFF2A viruses with anti-DAF renders viruses sensitive to human serum.

FIG. 4

Within the wild type retroviral genome gagpol and env protein coding sequences overlap within a region of 58bp (nucleotides 5777–5835). In packaging cells used today, gagpol and env are splitted on different chromosomes to reduce the risk of wild type formation. However, due to the intrinsic sequence homology recombination is still possible. In packaging cells based on fusion proteins like DAFF2A this sequence homology is eliminated, and recombination cannot take place.

REFERENCES

Bartholomew R. M. and Esser A. F. (1980) *Mechanism of antibody-independent activation of the first component of complement (C1) on retrovirus membranes* Biochemistry 19: 2847–2853

Brody B. A., Kimball M. G. and Hunter E. (1992) *Mutations within the transmembrane glycoprotein of Mason-Pfizer monkey virus: loss of SU-TM association and effects on infectivity* Virology 66: 3466–3475

Cooper N. R., Jensen F. C., Welsh R. M. and Oldstone M. B. A. (1976) *Lysis of RNA tumor viruses by human serum: direct antibody-independent triggering of the classical complement pathway* J. Exp. Med. 144: 970–984

Cosset F. L., Takeuchi Y., Battini J. L., Weiss R. A. and Collins M. K. L. (1995) *High-titer packaging cells producing recombinant retroviruses resistant to human serum* J. Virol. 69 (12): 7430–7436

Dorfman T., Mammano F., Haseltine W. A. and Göttlinger H. G. (1994) *Role of the matrix protein in the virion association of the human immunodeficiency virus type 1 envelope protein* J. Virol. 68: 1689–1696

Fodor W. L., Rollins S. A., Bianco-Caron S., Rother R. P., Guilmette E R., Burton W. V., Albrecht J.-C., Fleckenstein B. and Squinto S. P. (1995) *The complement control protein homolog of herpesvirus saimiri regulates serum complement by inhibiting C3 convertase activity* J. Virol. 69: 3889–3892

Rother R. P., Fodor W. L., Springhorn J. P., Birks C. W., Setter E., Sandrin M. S., Squinto S. P. and Rollins S. A. (1995) *A novel mechanism of retrovirus inactivation in human serum mediated by anti-Alpha-galactosyl natural antibody* J. Exp. Med. 182: 1345–1355

Rother R. P., Squinto S. P., Mason J. M. and Rollins S. A. (1995) *Protection of retroviral vector particles in human blood through complement inhibition* Hum. Gene Ther. 6: 429–435

Saifuddin M., Hedayati T., Atkinson J. P., Holguin M. E., Parker C. J. and Spear G. T. (1997) *Human immunodeficiency virus type 1 incorporates both glycosyl phosphatidylinositol-anchored CD5 and CD59 and integral CD46 at levels that protect from complement-mediated destruction* J. Gen. Virol. 78: 1907–1911

Takeuchi Y., Cosset F.-L. C., Lachmann P. J., Okada H., Weiss R. A. and Collins M. K. L. (1994) *Type C retrovirus inactivation by human complement is determined by both the viral genome and the producer cell* J. Virol. 68: 8001–8007

Takeuchi Y., Porter C. D., Strahan K. M., Preece A. F., Gustafsson K., Cosset F. L., Weiss R. A. and Collins M. K. L. (1996) *Sensitization of cells and retroviruses to human serum by (Alpha1–3) galactosyltransferase* Nature (London) 379: 85–88

Takeuchi Y., Porter C. D., Strahan K. M., Preece A. F., Gustafsson K., Cosset F. L., Weiss R. A. and Collins M. K. L. (1996) *Sensitization of cells and retroviruses to human serum by (Alpha1–3)galactosyltransferase* Nature (London) 379: 85–88

Welsh R. M., Cooper J. R., Jensen F. C. and Oldstone M. B. A. (1975) *Human serum lyses RNA tumour viruses* Nature (London) 257: 612–614

What is claimed is:

1. Single-stranded DNA (ssDNA) or double-stranded DNA (dsDNA) encoding a fusion protein of
   a retroviral surface protein (env) or a part thereof comprising its transmembrane domain, and
   a catalytically active domain of a complement inactivation factor.

2. Single-stranded DNA (ssDNA) or double-stranded DNA (dsDNA) according to claim 1, wherein the catalytically active domain of the complement inactivation factor is fused to a retroviral surface protein (env) or part thereof comprising its transmembrane domain.

3. Single-stranded DNA (ssDNA) or double-stranded DNA (dsDNA) according to claim 1, wherein the complement inactivation factor is a human complement activation factor selected from the group consisting of DAF, CD59, MCP or HRF; or a virus complement inactivation factor CCPH.

4. Single-stranded DNA (ssDNA) or double-stranded DNA (dsDNA) according to claim 1, wherein a retroviral extracellular surface domain (SU) protein, a retroviral transmembrane domain (TM) protein or parts thereof are selected from the group consisting of amphotropic env 10A1, env 4070A, ecotropic env, GALV env and chimeras thereof.

5. Single-stranded DNA (ssDNA) or double-stranded DNA (dsDNA) according to claim 1 offering a virus or a packaging cell, stability against a human complement system, and obtainable by subjecting said virus or said packaging cell comprising at least one fusion protein according to claim 1 to a human complement system, selecting said virus or said packaging cell which remains stable, and identifying and isolating said ssDNA or dsDNA from said virus or said packaging cell.

6. A fusion protein encoded by a ssDNA or dsDNA according to claim 1.

7. A virus stable against the human complement system comprising at least one fusion protein according to claim 1 and wherein at least one fusion protein is an envelope protein.

8. The virus according to claim 7, wherein the virus is selected from the group consisting of a retrovirus, a murine virus, a virus other than a retrovirus, a composite virus and a pseudotyped virus.

9. A packaging cell for the production of a virus according to claim 7 comprising integrated or unintegrated dsDNA.

10. A packaging cell according to claim 9, wherein the packaging cell is a human cell or a non-human cell, especially a murine cell.

11. The packaging cell according to claim 9 further comprising dsDNA encoding a wild-type retroviral envelope protein or a part thereof comprising a receptor interacting domain.

12. The packaging cell according to claim 9 selected from the group consisting of PA317 and GP+AM12.

13. A method of producing a virus stable against a human complement system for the enhancement of the transduction efficiency of the virus for gene therapy by fusing a retroviral surface protein (env) or part thereof comprising its transmembrane domain to the catalytically active domains of a complement inactivation factor.

14. The method according to claim 13, wherein the complement inactivation factor is a human complement activation factor selected from the group consisting of DAF, CD59, MCP and HRF and a virus complement inactivation factor CCPH.

15. The method according to claim 13, wherein a retroviral extracellular surface domain (SU) protein, a retroviral transmembrane domain (TM) protein or parts thereof, are selected from the group consisting of amphotropic env 10A1, env 4070A, ecotropic env, GALV env and chimeras thereof.

16. A method of producing a fusion protein by fusing a retroviral surface protein (env) or part thereof comprising its transmembrane domain to the catalytically active domain of a complement inactivation factor for the generation of complement resistant cells for transplantation.

17. A method of producing a fusion protein by fusing a retroviral surface protein (env) or part thereof comprising its transmembrane domain to the catalytically active domain of a complement inactivation factor for the reduction of the risk of the formation of replication competent viruses by means of packaging cells via recombination by eliminating the intrinsic sequence overlap of retroviral gagpol and env genes.

18. A method of producing a fusion protein by fusing a retroviral surface protein (env) or part thereof comprising its transmembrane domain to the catalytically active domain of a complement inactivation factor for generating complement stabilized packaging cells by coexpression of wild-type env proteins and fusion proteins.

19. A method of producing a fusion protein by fusing a retroviral surface protein (env) or part thereof comprising its transmembrane domain to the catalytically active domain of a complement inactivation factor for generating complement stabilized viruses.

20. The method according to claim 14, wherein the complement stabilized virus is selected from the group consisting of a retrovirus, a murine virus, a virus other than a retrovirus, a composite virus and a pseudotyped virus.

* * * * *